(12) United States Patent
Zaveri

(10) Patent No.: US 6,376,557 B1
(45) Date of Patent: Apr. 23, 2002

(54) METHODS FOR TREATING ALOPECIA

(76) Inventor: Chanda Bhuwalka Zaveri, 6740 Los Verdes Dr. #8, Rancho Palos Verdes, CA (US) 90275

( * ) Notice: Subject to any disclaimer, the term of this patent is extended or adjusted under 35 U.S.C. 154(b) by 0 days.

(21) Appl. No.: 09/526,921

(22) Filed: Mar. 16, 2000

(51) Int. Cl.⁷ .......................... A61K 47/00; A61K 33/04

(52) U.S. Cl. ...................... 514/880; 514/881; 514/937; 514/775; 424/705; 424/714

(58) Field of Search ................................ 514/880, 881, 514/937, 775; 424/705, 714

(56) References Cited

U.S. PATENT DOCUMENTS 5,641,480 A * 6/1997 Vermeer .................. 424/70.24

FOREIGN PATENT DOCUMENTS

| AT | 8932774 A | * | 11/1989 |
| CN | 1121696 A | * | 5/1996 |

OTHER PUBLICATIONS

Croda Product Information Brochure, 1999, www.croda.com.*
Exsymol Product Information Brochure, 1995, www.exsymol.com.*
Gary Null's Hair Care Products Brochure, 1998, www.naturalliving.com.*
"Health Disorder: Hair Loss", Homeocan, 1997, wwwhomeocan.ca.*
"Cosmetic Ingredients", Campo Research, 1997, www.campo-research.com.*
"A Taste of the Orient", Campo Reasearch, 1992, www-.campo-research.com.*

* cited by examiner

Primary Examiner—Zohreh Fay
Assistant Examiner—Brian-Yong S. Kwon
(74) Attorney, Agent, or Firm—Oppenheimer Wolff & Donnelly LLP

(57) ABSTRACT

Methods and compositions for the treatment of alopecia and the transdermal delivery of hair growth promoting agents. The compositions are formulated to be applied topically, preferably in the form of aqueous emulsions. The compositions may further include a variety of adjuvants to enhance the stability and effectiveness thereof.

8 Claims, No Drawings

METHODS FOR TREATING ALOPECIA

FIELD OF THE INVENTION

The present invention relates to compositions and methods for administering a hair growth promoter useful in the treatment of alopecia, as well as compositions and methods related to the stimulation of hair growth in animals.

BACKGROUND OF THE INVENTION

Hair loss and baldness (alopecia) are common phenomena in mammals, including humans. (See, for example, A. G. Messenger (1993) *J. Investing. Dermatol.* 101:48–98; D. G. Brodland, S. A. Muller (1991) Cutis 47:173–176; J. R. Spindler, J. L. Data (1992) *Dermatol. Nurs.* 4:93–99; A. K. C. Leung, W. L. M. Robson (1993) *J. Roy. Soc. Health* 113:252–256). Hair loss is an extremely common condition in healthy adult male humans, and also occurs frequently in adult female humans. In fact, some degree of alopecia on the vertex from puberty onwards is thought to be a universal phenomenon in both men and women (R. P. R. Dawber (1987) *Dermatologica* 175:23–28).

Hair loss may be naturally occurring (primary alopecia) or it may be induced by chemical or physical agents (secondary alopecia). (See, for example, M. B. Brodin (1987) *Dermatol. Clin.* 5:571–579; A. Tosti, et al. (1994) Drug Saf. 10:310–317; H. J. Carson, et al. (1994) *J. Cutan. Pathol.* 21:67–70). Alopecia is also frequently observed in both pre- and post-pubertal patients as a side effect of anti-cancer chemotherapy (A. M. Hussein, et al. (1990) Science 249:1564–1566; B. W. Cline (1984) *Cancer Nursinz* 7:221–228; A. F. Hood (1986) *Med. Clin. North Am.* 70:187–209). Hair loss may also result from specific disease states, such as mange, or formation of scar tissue from bites and with increasing age. (D. A. Mehregan, et al. (1992) *J. Am. Acad. Dermatol.* 27:935–942; D. A. Slagle, T. A. Martin (1991) *Am. Fam. Physician* 43:2019–2024; L. V. Spencer, J. P. Callen (1987) *Dermatol. Clin.* 5:565–570).

The physical phenomenon of hair loss may lead to psychological problems in the patient, decreased social activity, and the development of psychological diseases. In the case of cancer patients, the likelihood of chemotherapy-induced alopecia may lead to a refusal to accept treatment. As a result of the prevalence of alopecia, and its potentially devastating impact, there is immense interest in the development of effective clinical treatments, both to prevent hair loss and to stimulate regrowth of lost hair.

Despite the widespread occurrence of alopecia, the need for prevention and therapy, and extensive research efforts to find suitable remedies, there remains an urgent need for effective treatment. For example, lack of a proven and effective treatment for alopecia has caused many afflicted individuals to adopt the practice of wearing a wig or toupee. Another extreme measure used to combat alopecia, hair transplant surgery, is not available as an option in many cases, e.g., following chemotherapy, and offers, at best, only a partial remedy.

A common non-surgical treatment for stimulating hair growth which is currently used clinically is minoxidil (The Upjohn Company, Kalamazoo, Mich.). A solution of minoxidil as active ingredient is known as Rogain®. As stated in the Rogaine® Patient Information Booklet (The Upjohn Company, Kalamazoo, Mich., revised June, 1992) minoxidil is a vasodilatory drug which has serious side effects when administered orally for the treatment of hypertension. At the same time, topical application of minoxidil for the treatment of alopecia is only partially effective and suffers from a number of disadvantages. For example, it is only recommended for treatment of male pattern alopecia of the vertex (of frontal recession), has to be applied twice daily for at least four months, and requires a normal scalp with no local abrasions, dermatitis or sunburn—conditions that can increase absorption into the blood stream and the concomitant risk of side effects. Further, minoxidil is of limited effectiveness insofar as for those patients who do respond to minoxidil treatment, the new hair is likely to be shed within a few months after stopping treatment.

Moreover, it is recognized that delivering such active ingredient or ingredients through the skin, i.e., transdermally, as opposed to other methods of parenteral administration is extremely difficult. In this regard, in order to be effective, an active agent for hair treatment must pass through the outer layer of skin or epidermis and into the dermis layer before being absorbed into the bloodstream. The epidermis comprises two main parts, the stratum corneum and the stratum germinativum. The stratum corneum forms the outermost layer of the epidermis and consists of many stratified layers compacted, flattened, keratinized cells which have lost their nuclei. This outermost layer serves as a physical barrier to microorganisms and also to chemical agents. In particular, it behaves as a primary barrier to percutaneous absorption of drugs. Because of the barrier effect of the skin, it has heretofore only been possible to deliver drugs that are "low-dose" drugs, i.e. in the range of 15 mg/day or less, or those of low molecular weight. In addition, drugs for transdermal delivery must have the proper lipophilic-hydrophilic balance to permit adequate absorption. As early as the beginning of the twentieth century it has been known that lipid-soluble substances, such as non-electrolytes, have a comparatively greater skin permeability than water-soluble substances, such as electrolytes.

Recently, an orally-administered systemic agent, namely, finasteride, sold under the trademark Propecia® produced by Merck and Company of West Point, Penn., has proven clinically effective in treating alopecia in men with male pattern hair loss (androgenetic alopecia). Propecia® is a competitive and specific inhibitor of Type II 5α-reductase, an intracellular enzyme that converts the androgen testosterone into DHT. Administration of Propecia® decreases scalp and serum DHT concentrations and, by this mechanism, appears to interrupt the enzymatic pathway attributable to the development of androgenetic alopecia in those patients genetically predisposed to such condition.

While clinically effective in treating male pattern hair loss, Propecia® is known to produce significant adverse reactions. These adverse reactions include sexual dysfunction, as well as reported incidences of breast tenderness and enlargement. This composition is further extremely teratogenic and must not be handled by pregnant women insofar as Propecia® is suspected of causing impaired sexual organ development in male fetuses.

Accordingly, there is substantial need in the art for not only compositions that are effective at stimulating hair growth, but are further effective at transdermally delivering hair growth promoters useful in the treatment of alopecia. There is further a need in the art to provide a treatment for hair loss and compositions for delivering hair growth promoters useful in treating hair loss that are safe, simple, easy to apply and relatively inexpensive when compared to other hair loss treatments. There is a further need in the art to provide a treatment for hair loss that provides faster and more abundant hair regrowth than conventional treatments that additionally utilizes all natural ingredients that are non-toxic.

SUMMARY OF THE INVENTION

The present invention specifically addresses and alleviates the aforementioned deficiencies in the art. Specifically, the present invention is directed to compositions and methods useful for promoting hair growth when applied to an area of skin that is afflicted with alopecia, as well as compositions and methods useful in transdermally delivering hair growth promoting agents applied topically to the areas of skin afflicted with alopecia.

In a first preferred embodiment, the composition of the present invention comprises a suspension or aqueous emulsion having ancrine present in an amount from about 0.5% to about 4.0% by weight, capilectine present in an amount from about 1.2% to about 8.0% by weight, capisome present in an amount from about 1.2% to about 8.0% by weight, capigen present in an amount from about 1.2% to about 8.0% by weight, and capillisil present in an amount from about 3.0% to about 4.0% by weight, which is formulated to be applied topically.

In a second embodiment, the composition of the present invention comprises a suspension or aqueous emulsion having sulfur present from about 0.4% to about 5.0% by weight, mahanimba present from about 0.4% to about 5.0% by weight, malkagni present from about 0.3% to about 4.0% by weight, and Fitopur B present from about 1.2% to about 8.0% by weight, which is formulated to be applied topically.

In a third embodiment, the composition of the present invention comprises a suspension or aqueous emulsion having an mo le present from about 1.2% to about 8.0% by weight, biao beng li present from about 1.2% to about 8.0% by weight, qing hao present from about 1.2% to about 8.0% by weight, kui li present from about 1.2% to about 8.0% by weight, and enzymatic hydrolysate of casein present from about 0.3% to about 4.0% by weight, which is formulated to be applied topically.

In a fourth embodiment, the composition of the present invention comprises a suspension of aqueous emulsion having seamollient present at about 49.02% by weight, capilectine present at about 4.901% by weight, capigen present at about 4.901% by weight, ancrine present at about 2.45% by weight, Fitopur B present at about 4.901% by weight, sulfur present at about 3.431% by weight, capisome present at about 4.901% by weight, mahanimba present at about 3.431% by weight, capillisil present at about 1.961% by weight, malkagni present at about 1.961% by weight, kui li present at about 4.901% by weight, an mo le present at about 4.901%, biao beng li present at about 4.901% by weight, qing hao present at about 4.901% by weight, enzymatic hydrolysate of casein present at about 1.961% by weight, microreservoir present at about 1.471% by weight, and honeysuckle present at about 0.1% by weight, which is formulated to be applied topically.

Each of the aforementioned compositions of the preferred embodiments may further be useful for supporting and transdermally administering a pharmaceutically effective amount of hair growth promoter agent, such as minoxidil or propecia, insofar as such compositions attain superior transdermal penetration.

DETAILED DESCRIPTION OF THE PREFERRED EMBODIMENT

The detailed description set forth below is intended merely as a description of the presently preferred embodiment(s) of the invention, and is not intended to represent the only form(s) in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiment(s) that are also intended to be encompassed within the spirit and scope of the invention.

As set forth above, the compositions of the present invention comprise compositions, preferably in the form of a suspension or an aqueous emulsion, containing the indicated ingredients. With respect to a first preferred embodiment, those ingredients that are essential for accomplishing the desired results, namely, promoting hair growth when applied to an area of the skin that is afflicted with alopecia, are present in parts by weight within the following ranges:

TABLE 1

| COMPONENTS | GRAMS PER 1000 |
| --- | --- |
| Ancrine | 5 g to 40 g |
| Capilectine | 12 g to 80 g |
| Capisome | 12 g to 80 g |
| Capigen | 12 g to 80 g |
| Capillisil | 3 g to 40 g |

Ancrine is a complex available from Sederma, Inc. (Brooklyn, N.Y.) that comprises octyl butyrate and glutamine-containing peptides of plant origin that are substrates for transglutaminases.

Capilectine is a complex available from Sederma, Inc. (Brooklyn, N.Y.) that comprises a lectin derived from *Solanum tuberosum* and that exists in the form of a protein of molecular weight 21,000. The protein can exist in monomeric, dimeric, and trimeric forms that can be separated by methods such as polyacrylamide gel electrophoresis. The amino acid analysis of capilectine is as follows: 3.25% arginine, 4.25% serine, 11.5% aspartic acid, 12.5% glutamic acid, 4.0% threonine, 3.5% glycine, 19% alanine, 5.25% tyrosine, 3.75% proline, 1.0% methionine, 4.5% valine, 4.5% phenylalanine, 4.75% isoleucine, 5.75% leucine, 2.5% histidine, and 4.25% lysine.

Capisome is a liposome available from Sederma, Inc. (Brooklyn, N.Y.) that comprises: (1) homotaurine; (2) a bacterial filtrate of biotechnological origin from enterobacteria that contains high levels of peptides and the sulfur-containing amino acids methionine and cysteine; and (3) marine sulfopolysaccharides. The liposomes are small in size with a mean vesicle size of between 100 and 150 nm.

Capigen is a complex available from Sederma, Inc. (Brooklyn, N.Y.) that comprises three active constituents that have a complementary and synergistic action. The active constituents are homotaurine (3-aminopropane sulfonic acid), a bacterial filtrate obtained from a strain of microorganisms cultured in a specific medium comprising selected peptones, with the filtrate containing high levels of peptides, and a sulfomucopolysaccharide of marine origin, which is a complex of sulfated polysaccharides that are soluble in water and are found in the connective tissue and synovial fluids.

Capillisil is available from Exsymol S.A.M. of Monaco and is a 20% solution of dimethylsilanediol salicylate in butylene glycol with triethanolamine. It is obtained by mild hydrolysis of dimethylsilyl salicylate.

As will be recognized by those skilled in the art, such composition may be formulated as an aqueous suspension or an aqueous emulsion base according to any of a variety of formulations well known to those skilled in the art. For example, glyceryl stearate, other esters of glycerol with fatty acids, lanolin wax, lanolin alcohols, stearic acid, other high-molecular-weight carboxylic acids (fatty acids), mineral oil or paraffin may be utilized to constitute the oil phase of the emulsion which would be suitable for sustaining the aforementioned active ingredients. Other lipid-soluble components can also be used. Such other lipid-soluble components can include steareth-2; steareth-21; a branched-chain carboxylic acid ester of a branched-chain alcohol selected from the group consisting of isononyl isononanoate, isodecyl isononanoate, isooctyl isononanoate, isononyl isooctanoate, isodecyl isooctanoate, isooctyl isooctanoate, isononyl isodecanoate, isooctyl isodecanoate, and isodecyl isodecanoate; dimethicone; methylgluceth-20; hydrogenated vegetable oil; cetyl alcohol; squalane; a branched-chain neopentanoate selected from the group consisting of octyldodecyl neopentanoate, heptyldodecyl neopentanoate, nonyldodecyl neopentanoate, octylundecyl neopentanoate, heptylundecyl neopentanoate, nonylundecyl neopentanoate, octyltridecyl neopentanoate, heptyltridecyl neopentanoate, and nonyltridecyl neopentanoate; an arachidyl ester of a short-chain carboxylic acid selected from the group consisting of arachidyl propionate, arachidyl acetate, arachidyl butyrate, arachidyl isobutyrate, and mixtures thereof; a long-chain fatty acid ester of a medium-chain alcohol selected from the group consisting of octyl palmitate, octyl myristate, octyl stearate, heptyl palmitate, heptyl myristate, heptyl stearate, nonyl palmitate, nonyl myristate, nonyl stearate, and mixtures thereof; a myristyl ester of a long-chain fatty acid selected from the group consisting of myristyl myristate, myristyl laurate, myristyl palmitate, and mixtures thereof; bisabolol; hydrogenated jojoba oil; jojoba esters; a long-chain fatty ester acid of cetyl alcohol selected from the group consisting of cetyl palmitate, cetyl stearate, and cetyl myristate; and an arachidyl ester selected from the group consisting of arachidyl acetate, arachidyl propionate, arachidyl butyrate, and arachidyl isobutyrate. It should be further understood, however, that such agents are optional and that any of a variety of natural or naturally-deprived materials may be utilized as adjuvants, or may be dispensed with altogether.

In a second preferred embodiment, the invention comprises the following ingredients which are present in parts by weight within the following ranges:

TABLE 2

| COMPONENTS | GRAMS PER 1000 |
| --- | --- |
| Sulfur | 4 g to 50 g |
| Mahanimba | 4 g to 50 g |
| Malkagni | 3 g to 40 g |
| Fitopur B | 12 g to 80 g |

Mahanimba is an extract of the flowers and inflorescence of the neem tree (*Melia azadirachta*) and contains carotenoids, amino acids, phytosterols, mucins, polyacetylenes, and sesquiterpenes. The neem tree is used for many traditional medicinal uses in the Indian subcontinent.

Malkagni is an extract of the seeds, leaves, and flowers of the intellect tree (*Celastrus paniculata*) and contains tannins, mineral salts, saponins, and iridic glycosides. The intellect tree is also used for many medicinal purposes in the Indian subcontinent.

Fitopur B is a complex available from Sederma, Inc. (Brooklyn, N.Y.) and comprises extracts of three plants: buchu (*Buchu barosma*), henna (*Lawsonia inermis*), and venus hair (*Adiantium capillus-veneris*). The essential oil of buchu contains the terpenic oil diosphenol and sulfur compounds. The leaves of henna contain flavonic pigments including luteoline and laxanthones, principally lawsone. Venus hair is a small fern native to the south of France; it has diuretic and emollient activity. Fitopur B is a clear solution of light beige color preserved with 0.2% mixed parabens and 0.1% potassium sorbate, and has a pH of 6.9 and a density of about 1.01 g/cm$^3$.

As discussed above, the components may be formulated as an aqueous emulsion or, alternatively, may be simply formulated from the ingredients themselves.

According to a third preferred embodiment, the composition of the present invention comprises, in percent by weight, the following ingredients:

TABLE 3

| COMPONENTS | GRAMS PER 1000 |
| --- | --- |
| An Mo Le | 12 g to 80 g |
| Biao Beng Li | 12 g to 80 g |
| Qing Hao | 12 g to 80 g |
| Kui Li | 12 g to 80 g |
| Enzymatic Hydrolysate of Casein | 3 g to 40 g |

An mo li is an extract of the whole fruits, seeds, and skins, as well as the leaves of *Spondias amara* and contains amino acids, histamine, acetylcholine, carotenoids, and chlorophyll. It has been commonly used in Chinese medicine. The extract is a clear light brown liquid and contains 25% propylene glycol.

Biao beng li is an extract of the berries of *Rubus thunbergii*, and contains flavonoids, procyanidines, amino acids, and phytosterols. Biao beng li is commonly used in cosmetics and medical applications in the Orient. The extract is a clear, light brownish red liquid and contains 34% propylene glycol.

Qing hao is an extract of the aerial parts of the Chinese wormwood plant (*Artemisia apiacea*), and contains qinghaosu, flavonoids, polysaccharides, essential oils, and amino acids. Qing hao is commonly used for cosmetics and medical applications in Oriental medicine. The extract is a clear, light brown to yellow liquid and contains 40% 1,3-butylene glycol.

Kui li is an extract of the whole herb with roots of the Oriental maiden hair plant (*Trichomonas japonica*) and contains saponins, flavonoids, essential oils, and phytosterols. Kui li is commonly used for cosmetic applications in Oriental medicine. The extract is a clear, light yellowish brown liquid that contains 35% propylene glycol.

Enzymatic hydrolysate of casein is a hydrolysate of the milk protein casein produced by enzymatic hydrolysis. The enzymatic hydrolysate of casein has a pH of 4.6±0.5 and is soluble in water at up to 10% concentration. Enzymatic hydrolysate of casein is a hair care additive that repairs transversal splitting, split ends, and defibration from dyeing and permanent waves. It is compatible with usual shampoo ingredients and is also compatible with cationic substances. A suitable source of enzymatic hydrolysate of casein is Vevy Europe S.p.A. of Genoa, Italy, who markets enzymatic hydrolysate of casein under the name "EPCH."

As with the other embodiments, the composition of the present invention according to the third preferred embodiment may be formed as a suspension or aqueous emulsion. In addition, it will be recognized by those skilled in the art that adjuvants may be added to further enhance and stabilize the basic components identified in any of the embodiments, which may include silicone fluids, lipids or lipid-soluble components, buffering agents, preservatives, chelating agents, antioxidants and/or antimicrobial agents.

According to yet a fourth preferred embodiment, the composition of the present invention comprises the following components, in percent by weight, encompassing the following ranges:

TABLE 4

| COMPONENTS | GRAMS PER 1000 |
| --- | --- |
| Seamollient | 490.20 base |
| Capilectine | 49.01 |
| Capigen | 49.01 |
| Ancrine | 24.50 |
| Fitopur B | 49.01 |
| Sulfur | 34.31 |
| Capisome | 49.01 |
| Mahanimba | 34.31 |
| Capillisil | 19.61 |
| Malkagni | 19.61 |
| Kui Li | 49.01 |
| An Mo Le | 49.01 |
| Biao Beng Li | 49.01 |
| Qing Hao | 49.01 |
| EPCH | 19.61 |
| Microreservoir | 14.71 |
| Honeysuckle | 1.0 |

Seamollient is available from Philip Rockley, Ltd. (East Setauket, N.J.) and is an extract of Hawaiian sea plants that acts as an emollient and moisturizer. It contains chlorphenesin, phenoxyethanol, propylene glycol, and sodium dehydroacetate as preservatives.

Microreservoir is an inert particle that has a large interspatial volume that can adsorb active components and hold it to the skin or the scalp. It is marketed by Sederma. It is a vesicle made of lamellar membranes organized as double phospholipid layers with a diameter of less than 200 nm and containing palmitoylcarnitine to cause them to have a timed-release effect.

With respect to each of the aforementioned embodiments, it should be understood that the percentages of the various components thereof will total one hundred percent by weight and if other materials are included in the formulation, the percentages of all ingredients will total one hundred percent by weight.

As to the method of administering the aforementioned compounds to optimally treat alopecia, such compositions should be applied topically to the area of skin afflicted with alopecia at least two times per day.

Moreover, it should be understood that in order to preserve the restored hair growth to the skin previously afflicted with alopecia, it will be necessary to continue utilizing such formulations according to such regimens indefinitely, or until such time as the subject area of alopecia need no longer be treated.

In addition to the foregoing it should be expressly understood and recognized by those skilled in the art that the aforementioned compositions may be suitable for administering other hair growth promoting agents, such as minoxidil, insofar as such compositions exhibit superior transdermal penetration. When used in such applications, it will be understood that additional adjuvants may be added to preserve the active ingredients incorporated therewith, which may include buffers, antioxidants, antibacterial agents, preservatives, chelating agents, and the like. Buffers include, but are not limited to, phosphate and tris (hydroxyaminomethane) ("Tris"). Chelating agents include, but are not limited to, EDTA. Antibacterial agents and preservatives include, but are not limited to, methylparaben, ethylparaben, propylparaben, butylparaben, chlorphenesin, phenoxyethanol, diazolidinyl urea, and sodium dehydroacetate.

The composition can further include other ingredients, such as vitamins, panthenol, hyaluronic acid, other proteins, other plant extracts, a thickener component, a sunscreen, colorant, and fragrance. A number of sunscreens are well known in the art, including octylmethoxycinnamate, p-amino benzoic acid, ethyl p-aminobenzoate, isobutyl p-aminobenzoate, glyceryl p-amino benzoate, p-dimethylaminobenzoic acid, methyl anthranilate, menthyl anthranilate, phenyl anthranilate, benzyl anthranilate, phenylethyl anthranilate, linalyl anthranilate, terpinyl anthranilate, cyclohexenyl anthranilate, amyl salicylate, phenyl salicylate, benzyl salicylate, menthyl salicylate, glyceryl salicylate, dipropyleneglycol salicylate, methyl cinnamate, benzyl cinnamate, α-phenyl cinnamonitrile, butyl cinnamoylpyruvate, umbelliferone, methylacetoumbelliferone, esculetin, methylesculetin, daphnetin, esculin, daphnin, diphenylbutadiene, stilbene, dibenzalacetone, benzalacetophenone, sodium 2-naphthol-3,6-disulfonate, sodium 2-naphthol-6,8-disulfonate, dihydroxynaphthoic acid, salts of dihydroxynaphthoic acid, o-hydroxybiphenyldisulfonates, 7-hydroxycoumarin, 7-methylcoumarin, 3-phenylcoumarin, 2-acetyl-3-bromoindazole, phenylbenzoxazole, methylnaphthoxazole, arylbenzothiazoles, quinine bisulfate, quinine sulfate, quinine chloride, quinine oleate, quinine tannate, 8-hydroxyquinoline salts, 2-phenylquinoline, hydroxy-substituted benzophenones, methoxy-substituted benzophenones, uric acid, vilouric acid, tannic acid, tannic acid hexaethylether, hydroquinone, oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, and etocrylene.

The composition is prepared by standard mixing techniques such as are conventional for blending lipid-soluble components and water-soluble components. These mixing techniques include both manual and mechanical mixing, and include homogenization mixing and sweep mixing. The mixing techniques to be used can be chosen by one of ordinary skill in the art based on variables such as the viscosity of the components to be mixed and the volume of those components, as well as the relative proportion of lipid-soluble and water-soluble ingredients. The composition can be mixed in two or more batches, such as one batch containing lipid-soluble ingredients and another batch containing water-soluble ingredients, and the batches can then be mixed at the final stage of preparation.

Although the invention has been described herein with specific reference to a presently preferred embodiment thereof, it will be appreciated by those skilled in the art that various additions, modifications, deletions and alterations may be made to such preferred embodiment without departing from the spirit and scope of the invention. Accordingly, it is intended that all reasonably foreseeable additions, modifications, deletions and alterations be included within the scope of the invention as defined in the following claims.

What is claimed is:

1. A method for treating hair loss resulting from alopecia which comprises topically applying to the skin at a desired area for hair regrowth an effective amount of a composition comprising a complex comprising octyl butyrate and glutamine-containing peptides, a lectin derived from *Solanum tuberosum*, a liposome with a mean vesicle size of between 100 and 150 nm comprising homotaurine, a bacterial filtrate from enterobacteria that contains high levels of peptides and methionine and cystine, and marine sulfomucopolysaccharides, a complex comprising homotaurine, a bacterial filtrate, and sulfomucopolysaccharides, and a 20% solution of dimethylsilanediol salicylate in butylene glycol with triethanolamine.

2. The method of claim 1 wherein in said composition said complex comprising octyl butyrate and glutamine-containing peptides is present from about 0.5% to about 4.0% by weight, said lectin derived from *Solanum tuberosum* is present from about 1.2% to about 8.0% by weight, said liposome with a mean vesicle size of between 100 and 150 nm comprising homotaurine, a bacterial filtrate from enterobacteria that contains high levels of peptides and methionine and cystine, and marine sulfomucopolysaccharides is present from about 1.2% to about 8.0% by weight, said complex comprising homotaurine, a bacterial filtrate, and sulfomucopolysaccharides is present from about 1.2% to about 8.0% by weight, and said 20% solution of dimethylsilanediol salicylate in butylene glycol with triethanolamine is present from about 3.0% to about 4.0% by weight.

3. A method for treating hair loss resulting from alopecia which comprises topically applying to the skin at a desired area for hair regrowth an effective amount of a composition comprising sulfur, mahanimba, malkagni, and a complex comprising extracts of buchu, henna, and venus hair.

4. The method of claim 3 wherein in said composition said sulfur is present from about 0.4% to about 5.0% by weight, said mahanimba is present from about 0.4% to about 5.0% by weight, said malkagni is present from about 0.3% to about 4.0% by weight, and said complex comprising extracts of buchu, henna, and venus hair is present from about 1.2% to about 8.0% by weight.

5. A method for treating hair loss resulting from alopecia which comprises topically applying to the skin at a desired area for regrowth an effective amount of a composition comprising an mo le, biao beng li, qing hao, kui li, and enzymatic hydrolysate of casein.

6. The method of claim 5 herein in said composition said an mo le is present from about 1.2% to about 8.0% by weight, said biao beng li is present from about 1.2% to about 8.0% by weight, said qing hao is present from about 1.2% to about 8.0% by weight, said kui li is present from about 1.2% to about 8.0% by weight, and said enzymatic hydrolysate of casein is present from about 0.3% to about 4.0% by weight.

7. A method for treating hair loss resulting from alopecia which comprises topically applying to the skin at a desired area for hair regrowth an effective amount of a composition comprising an extract of Hawaiian sea plants, a lectin derived from *Solanum tuberosum*, a complex comprising homotaurine, a bacterial filtrate, and sulfomucopolysaccharides, a complex comprising octyl butyrate and glutamine-containing peptides, a complex comprising extracts of buchu, henna, and venus hair, sulfur, a liposome with a mean vesicle size of between 100 and 150 nm comprising homotaurine, a bacterial filtrate from enterobacteria that contains high levels of peptides and methionine and cystine, and marine sulfomucopolysaccharides, mahanimba, a 20% solution of dimethylsilanediol salicylate in butylene glycol with triethanolamine, malkagni, kui li, an mo le, biao beng li, qing hao, enzymatic hydrolyzate of casein, a vesicle made of lamellar membranes organized as double phospholipid layers with a diameter of less than 200 nm and containing palmitoylcarnitine, and honeysuckle.

8. The method of claim 7 wherein in said composition said extract of Hawaiian sea plants is present at about 49.02% by weight, said lectin derived from *Solanum tuberosum* is present at about 4.901% by weight, said complex comprising homotaurine, a bacterial filtrate, and sulfomucopolysaccharides is present at about 4.901% by weight, said complex comprising octyl butyrate and glutamine-containing peptides is present at about 2.45% by weight, said complex comprising extracts of buchu, henna, and venus hair is present at about 4.901% by weight, said sulfur is present at about 3.431% by weight, said liposome with a mean vesicle size of between 100 and 150 nm comprising homotaurine, a bacterial filtrate from enterobacteria that contains high levels of peptides and methionine and cystine, and marine sulfomucopolysaccharides is present at about 4.901% by weight, said mahanimba is present at 3.431% by weight, said 20% solution of dimethylsilanediol salicylate in butylene glycol with triethanolamine is present at about 1.961% by weight, said malkagni is present at about 1.961% by weight, said kui li is present at about 4.901% by weight, said an mo le is present at about 4.901% by weight, said biao beng li is present at about 4.901% by weight, said qing hao is present at about 4.901% by weight, said enzymatic hydrolysate of casein is present at about 1.961% by weight, said a vesicle made of lamellar membranes organized as double phospholipid layers with a diameter of less than 200 nm and containing palmitoylcarnitine is present at about 1.471% by weight, and said honeysuckle is present at about 0.1% by weight.

* * * * *